United States Patent
Paxia et al.

(10) Patent No.: US 9,390,163 B2
(45) Date of Patent: Jul. 12, 2016

(54) METHOD, SYSTEM AND SOFTWARE ARRANGEMENT FOR DETECTING OR DETERMINING SIMILARITY REGIONS BETWEEN DATASETS

(75) Inventors: Salvatore Paxia, New York, NY (US); Bhubaneswar Mishra, Great Neck, NY (US); Yi Zhou, Shanghai (CN)

(73) Assignee: New York University, New York, NY (US)

( * ) Notice: Subject to any disclaimer, the term of this patent is extended or adjusted under 35 U.S.C. 154(b) by 1071 days.

(21) Appl. No.: 11/410,692

(22) Filed: Apr. 24, 2006

(65) Prior Publication Data
US 2008/0046187 A1 Feb. 21, 2008

Related U.S. Application Data

(60) Provisional application No. 60/674,009, filed on Apr. 22, 2005.

(51) Int. Cl.
| | |
|---|---|
| *G01N 33/48* | (2006.01) |
| *G01N 33/50* | (2006.01) |
| *G06F 17/30* | (2006.01) |
| *G06F 19/12* | (2011.01) |
| *G06F 19/24* | (2011.01) |
| *G06F 19/26* | (2011.01) |
| *G06F 19/22* | (2011.01) |

(52) U.S. Cl.
CPC .......... *G06F 17/30675* (2013.01); *G06F 19/12* (2013.01); *G06F 19/24* (2013.01); *G06F 19/26* (2013.01); *G06F 19/22* (2013.01)

(58) Field of Classification Search
None
See application file for complete search history.

(56) References Cited

U.S. PATENT DOCUMENTS

| | | | |
|---|---|---|---|
| 6,221,592 B1 * | 4/2001 | Schwartz et al. | 435/6 |
| 6,643,634 B2 * | 11/2003 | Koleszar et al. | 707/1 |

FOREIGN PATENT DOCUMENTS

| | | | |
|---|---|---|---|
| WO | WO 02/26934 | * | 4/2002 |

OTHER PUBLICATIONS

Kuzmanovski et al. Optimization of artificial neural networks for prediction of the unit cell parameters in orthorhombic perovskites. Comparison with multiple linear regression. Chemometrics and Intelligent laboratory Systems, vol. 67, 2003, pp. 167-174.*

(Continued)

*Primary Examiner* — Russell S Negin
(74) *Attorney, Agent, or Firm* — Andrews Kurth LLP (57) ABSTRACT

Methods, systems, and computer-readable media are provided which can identify and provide local variations in regions of similarity among two or more data sets. These data sets may be represented as sequences such as, e.g., genomic sequences or words in a text. The local variations in similarity levels can be provided by selecting an initial prior distribution relating the data sets, organizing the first data set into windows and the remaining data sets into blocks, using the priors to sample one or more sets of words from the first data set, computing a similarity curve from exact and inexact matches for these words and, if convergence of results is not achieved, computing a new set of priors and repeating the sampling and computation of similarity curves. The computations can be performed using an amount of computational time that is linearly proportional to the size of the data sets.

43 Claims, 2 Drawing Sheets

(56) References Cited

OTHER PUBLICATIONS

Wu et al. Statistical measures of DNA sequence dissimilarity under Markov chain models of base composition. Biometrics. Jun. 2001, vol. 57, pp. 441-448; online version has pages numbers from 1-16 with two p. 1's.*

Anderson et al. Introduction to Statistics: Concepts and Applications, Second Edition. New York: West Publishing Company, 1991. pp. 219-222.*

Leydesdorff L. The triple helix: an evolutionary model of innovations. Research Policy, 2000, vol. 29, pp. 243-255.*

Correlation, 2003, 2 pages. The Penguin Dictionary of Economics. Retrieved online on Dec. 2, 2012 from <<http://www.credoreference.com/entry/penguincon/correlation>>.*

Zhang et al. Fission yeast gene structure and recognition. Nucleic Acids Research, vol. 22, 1994, pp. 1750-1759.*

* cited by examiner

METHOD, SYSTEM AND SOFTWARE ARRANGEMENT FOR DETECTING OR DETERMINING SIMILARITY REGIONS BETWEEN DATASETS

CROSS-REFERENCE TO RELATED APPLICATION(S)

This application claims priority from U.S. Patent Application No. 60/674,009, filed Apr. 22, 2005, the entire disclosure of which is incorporated herein by reference.

GOVERNMENTAL SUPPORT

The research leading to the present invention was supported, at least in part, by the National Science Foundation under Grant number CCR-0325605, and by DARPA under Grant no. F30602-01-2-0556. Thus, the U.S. government may have certain rights in the invention.

FIELD OF THE INVENTION

The present invention relates to an efficient method, system and software arrangement for comparing two or more long strings of characters with "almost common" subsequences interspersed. Examples of such strings of characters may include genome sequences of nucleotides, shorter sequences of amino acids, natural-language texts, natural or computer-generated texts or hypertexts, weblogs or "blogs," network logs, scripts or object code encoding computer procedures that may have been successively revised, plagiarized texts, etc.

BACKGROUND INFORMATION

Comparisons of large sets of data to detect regions of similarity among them has many practical applications. For example, natural-language word sequences appearing in stories, articles, term papers, etc., may be compared to determine whether material has been copied or plagiarized from one to another. Computer code listings can be compared to assess whether or not code in one listing has been copied from another listing. In the fields of biology and bioinformatics, sequences of genes, nucleotides, amino acids, etc., that appear in different biological structures may be compared to detect if homology exists that can indicate similar biological functions or that the sequences are related to a common origin.

Sequence alignment tools have incorporated many innovations to greatly advance detailed comparative genomics studies. For example, recent segmental duplications in mammalian genomes (with identity level >90%) can be detected using BLAST or other sequence alignment tools.

However, many of these tools used in genomic applications may use exact or inexact k-mers as homology seeds for local alignment extension. Thus there may be a compromise between sensitivity and computational efficiency when they are used to detect homologous segments, segmental duplications, or homology-based phylogenic distances, as homology levels become lower.

To improve sensitivity, many of these tools rely on exhaustive searches of exact matches with short mers or inexact matches with longer mers. This approach can yield a large number of false-positives, which may require subsequent post-processing filtering, which can be expensive. Alternatively, more stringent search criteria (e.g., longer mers with more exact matches) can be used to improve efficiency. However, these algorithms may fail to detect low-homology regions such as, for example, ancient duplication events. In order to detect less-recent duplications, orthologous genes have been used as "anchors" to map out duplication blocks. However, this approach may not be suitable for identifying duplications that are not subject to a strong selection process, e.g., sequences containing only non-coding regions.

SUMMARY OF THE INVENTION

One object of the present invention is to provide a system, a method, a software arrangement, and a computer-accessible medium (hereinafter collectively referred to as "PRIZM") for efficiently and robustly detecting or identifying variations in similarity among two or more sets of data, which may be in the form of sequences. Similar regions between two sequences can be efficiently determined even when the similarity level drops to a value around 65%. In genomics applications, algorithms may be employed that incorporate background knowledge about genome evolution. For example, information relating to expected statistical distributions of similarity variations among the sets of data can be used. This information can be domain-dependent, and it can be based on the nature of the data sets being analyzed, or on a statistical model. This information may be in the form of a statistical prior distribution, a hierarchal prior model, a uniform distribution, a similarity curve, or a homology curve. A variety of priors may be used such as, e.g., a noninformative improper prior, an exponential prior, a Gamma prior, or a prior based on a Juke-Cantor one-parameter evolution model or a Kimura two-parameter evolution model. These priors may reflect statistical models based on, e.g., mutations or edit operations. The results obtained may be generally unaffected by the choice of a particular prior, while the computational efficiency may be only mildly affected by this choice. The time required to perform the computations can be linearly proportional to the size of the data sets.

In certain exemplary embodiments of the present invention, PRIZM can process multiple sequences, and the similarity regions between a given sequence and a set of other sequences may be determined. A sequence of rearrangement events and a rough estimation of the time of these rearrangements may also be computed. In addition, exemplary embodiments of the present invention can be applied to analyze other domains by establishing appropriate priors.

In further exemplary embodiments of the present invention, a Bayesian scheme can be used to refine parameters and priors used to converge similarity results to a desired degree of accuracy. A boosting technique may be used in conjunction with the Bayesian scheme.

In exemplary embodiments of the present invention, regions of predetermined similarity and/or local alignment data may be identified with respect to two or more data sets.

In still further exemplary embodiments of the present invention, similarity may be detected in comparative genomics, genome sequences of nucleotides, shorter sequences of amino acids, natural-language texts, natural or computer-generated texts or hypertexts, network logs, scripts or object code encoding computer procedures that may have been successively revised, code listings for webpages, weblogs, sets of time-series data, speech data, image data, video data, plagiarized texts, etc.

In certain exemplary embodiments of the present invention, regions of predetermined similarity and/or variations in similarity across regions can be determined using exact and/or inexact matches. Inexact matches can include matches that include one error or two errors between compared regions or subregions of the sets of data. Subregions of the sets of data can be selected for comparison based on expected statistical distributions of similarity variations. Subregions can be organized as sets of blocks and/or windows, and the blocks can be stored in the form of, e.g., a hash table or a suffix array.

In exemplary embodiments of the present invention, an iterative process may be used to obtain accurate determinations of variations in similarity regions and/or regions of predetermined similarity among data sets. Results of a calculated comparison may be used to modify or refine parameters or models associated with information relating to expected statistical distributions of similarity variations, and the comparisons may again be computed using the modified or refined information. This iterative process can be continued until specified condition is met. The condition can include, e.g., a preselected number of iterations or total computational time, or a convergence of the similarity calculations to a uniform result to a preselected degree of accuracy.

These and other objects, features and advantages of the present invention will become apparent upon reading the following detailed description of embodiments of the invention, when taken in conjunction with the appended claims.

BRIEF DESCRIPTION OF THE DRAWINGS

Further objects, features and advantages of the invention will become apparent from the following detailed description taken in conjunction with the accompanying figures showing illustrative embodiments of the invention, in which.

DETAILED DESCRIPTION OF EXEMPLARY EMBODIMENTS

The method, system and software arrangement according to an exemplary embodiment of the present invention is capable of generating a function called a "similarity curve" based on two sequences. The value of this function at a location on a first sequence can be selected as the highest local similarity level of a short region straddling that location, when compared with a second sequence. Certain characteristics related to this curve such as, e.g., its structure, a distribution of similarities across the entire first sequence, a correlation between the curve and a composition of the underlying regions (e.g., coding vs. noncoding, CG-content, stability or flexibility), etc. can provide information describing how the two sequences are related in terms of, for example, evolutionary distances, patterns of conservation, and/or mechanisms of evolution and selection that have acted since their divergence.

A location can be provided in a first sequence, $G_1[\alpha]$, and a short window $W_{1,\alpha} = G_1[\alpha, \alpha+m-1]$ can be specified starting at $\alpha$. This window can be compared with a word of equal length from the second sequence starting at $G_2[\beta]$, e.g., $W_{2,\beta} = G_2[\beta, \beta+m-1]$. The similarity level may be defined for the locations $G_1[\alpha]$ and $G_2[\beta]$ and a window as $$h^{(2)}(G_1[\alpha], G_2[\beta], m) = \frac{1}{m} \sum_{\gamma=0}^{m-1} \begin{cases} 1 & G_1[\alpha+\gamma] = G_2[\beta+\gamma] \\ 0 & \text{otherwise} \end{cases}$$

The highest similarity level for the sequence $G_1$ at position $\alpha$ as computed with respect to $G_2$ can be denoted by $h(\alpha)$, which may be expressed as:

$$h(\alpha) = \max_{1 \leq \beta < |G_2| - m} h^{(2)}(G_1[\alpha], G_2[\beta], m)$$

The "similarity curve" for the first sequence, $G_1$ with respect to the second sequence $G_2$ may then be defined as:

$h: G_1[\alpha \ldots \alpha+m-1] \to [0,1]$ $\alpha \mapsto h(\alpha)$

Low-similarity alignments may be detected without a quadratic number of pair-wise inter-sequence inexact searches, even when verification of a low-homology match is relatively easy. That is, the correctness of a given similarity mapping between two sequences can be verified in a linear amount of time, even if the similarity levels are quite low. Thus, while a deterministic version with sub-quadratic complexity may not be achievable, a linear-time non-deterministic algorithm exists.

In exemplary embodiments of the present invention, a non-deterministic technique can be replaced with a probabilistic estimation scheme, where probabilistic distributions employed therein can be based on, e.g., biologically meaningful priors. This scheme can include repetition of the following steps until convergence is achieved:
  a) provide an estimated probabilistic distribution;
  b) compute a linear-time verification; and
  c) refine the probabilistic distribution for a successive iteration.

For example, a Bayesian scheme optionally combined with a boosting technique can be used to modify the probabilistic distributions provided in step (a) above from one iteration to the next. For each iteration, a set of words with a specific distribution may be selected from one sequence, and can be optimally partitioned into groups for "in silico experiments" involving an exact-match search, an inexact-match search with one error, an inexact match search with two errors, etc. These searches can be conducted efficiently over the second sequence, particularly if the second sequence has been pre-processed and stored in an efficient data structure (e.g., as a suffix array or a hash table). Based on these calculations, a Bayesian estimator can compute the local similarity levels for the second sequence, and use it to verify and refine the probabilistic distributions for the next iteration. In this manner, convergence to the true local similarity levels may be achieved after only a few iterations.

Exemplary embodiments of the present invention are described in more detail as follows:

Prespecified parameters b, $B = |G_2|/b$, w, m, and $N_0$, $N_1, \ldots, N_k$ ($k \leq m$) may be defined, where k may be preferably set equal to 2. A set of k+1 m-mers $S_0, \ldots, S_k$ may be selected randomly (uniformly with replacement) from $G_1[\alpha, \alpha+w-1]$ such that $|S_0| = N_0, |S_1| = N_1, \ldots,$ and $|S_k| = N_k$.

An m-mer can be understood to represent a word of length m, which may be selected from either sequence.

A block in the second sequence of length b may be identified as $B_\beta \equiv G_2[\beta, \beta+b-1]$. The parameter $X_i$ (i=0 to k) may be defined as the number of corresponding m-mers $S_i$ (i=0 to k) that match exactly (with one, two, etc. up to k mismatches, respectively) to an m-mer in $G_2[\beta, \beta+b-1]$. The values of $X_i$ for $0 \leq i \leq k$ can thus represent binomially distributed random variables whose parameters depend on the similarity level h.

The local similarity may be estimated by the following robust estimators:

$$\langle h | X_0, X_1, \ldots, X_k \rangle = \int_0^1 h p(h | X_0, X_1, \ldots, X_k) dh.$$

The mean, standard deviation and confidence of the similarity function over $B_\beta$ may also be determined. The parameter $\beta^*$ can be defined as $\arg\max_\beta \text{mean}(B_\beta)$. The similarity function can then be estimated at $\alpha$ by the value mean ($B_{\beta^*}$).

To create a robust estimator, it may be preferable to select a prior for p(h). A simple choice for this would be a uniform prior such as, e.g., p(h)=1, $0 \leq h \leq 1$, or a slightly modified uniform prior, e.g., p(h)=4/3, $\frac{1}{4} < h \leq 1$. These exemplary priors are uninformative and may be less restrictive. Another improper prior that may be preferable is, e.g., p(h)=$\lambda$Exp[$-\lambda h$], $0 \leq h \leq 1$. Other parametric priors, which may have an evolutionary explanation, can be created by applying a general theorem.

Several criteria may be used to detect convergence of the algorithm, at which point the processing operations may be stopped. For example, the processing may be interrupted once a predefined level of detail is obtained. Alternatively, a predetermined amount of time or a predetermined number of iterations can be selected for application of the algorithm. Processing may also be halted if calculated similarity estimates differ by less than a predetermined amount from the similarity curve computed at the previous step.

Detailed local alignment may be obtained by using the local similarity information, the pre-processed data structure, and a local alignment procedure/tool.

In iteration i, an interval I with k similarity estimates may be expressed as:

$$\langle \mu_1, \sigma_1 \rangle, \langle \mu_2, \sigma_2 \rangle, \ldots, \langle \mu_k, \sigma_k \rangle$$

An updated prior may be determined using a heuristic argument, based on a weighted average of the estimated parameters. Normal random variables $x_i$, i=1 to k, may be defined as $$x_1 = \mu_1 + \sigma_1 N(0,1)$$

$$x_2 = \mu_2 + \sigma_2 N(0,1)$$

$$\ldots$$

$$x_k = \mu_k + \sigma_k N(0,1).$$

A weighted average of these variables may be written as follows:

$$X_I = \omega_1 x_1 + \omega_2 x_2 + \ldots + \omega_k x_k,$$

where the $\omega_j$ parameter can be a normalized weighting factor such that $\omega_1 + \omega_2 + \ldots + \omega_k = 1$. Thus $$X_I = \sum_j \omega_j \mu_j + \sum_j \omega_j \sigma_j N(0,1)$$

$$\approx N(\mu_I, \sigma_I)$$

If each weighting factor $\omega_j$ is selected to be inversely proportional to the standard deviation of the corresponding normal random variables $x_j$, i.e., $$\omega_j = \frac{\sum_j (\sigma_j)^{-1}}{\sigma_j},$$

then it can be shown that $$\mu_I = \frac{\sum_j \mu_j (\sigma_j)^{-1}}{\sum_j (\sigma_j)^{-1}} \text{ and } \sigma_I^2 = \frac{k^2}{\left(\sum_j (\sigma_j)^{-1}\right)^2}$$

The distribution for an interval I may be approximated by $p_{i,1}(h) \approx N(\mu_1 \sigma_1)$. The parameter $p_{0,G}$=p(h) may be set equal to the initial prior chosen above.

A prior may also be refined by the choice of a convex combination determined by a parameter $0 < \delta \leq 1$, e.g.:

$$p_{i,1}(h) = (1-\delta) p_{0,G}(h) + \delta(\mu_1 + \sigma_1 N(0,1)).$$

Parameters may be optimized in several ways. For example, the number of blocks (b) and the number of windows (w) may be chosen a priori based on a selected resolution for similarity. These parameters may be selected such that b=O($\sqrt{G_2}$) and w=O($\sqrt{G_1}$). An amount of work K=O(1) may be assigned to a region defined by a combination of any single block with any single window. Thus the amount of work may be expressed as approximately $K(G_1 G_2)/(wb)$=O$(G_1 + G_2)$ per iteration.

The mer size parameter m may be selected such that the probability of a match or "hit" in a block containing a similarity sequence is much higher than in a random block, i.e., $$(b/4^m) << E(h_{0,G})^m.$$

The similarity curve between a sequence $S_1$ and a set of n sequences $T_1, \ldots, T_n$, may also be determined by applying the procedures described above to the sequence $S_1$ and a new sequence $S_2$ obtained by concatenating $T_1, \ldots, T_n$.

Figure 1:
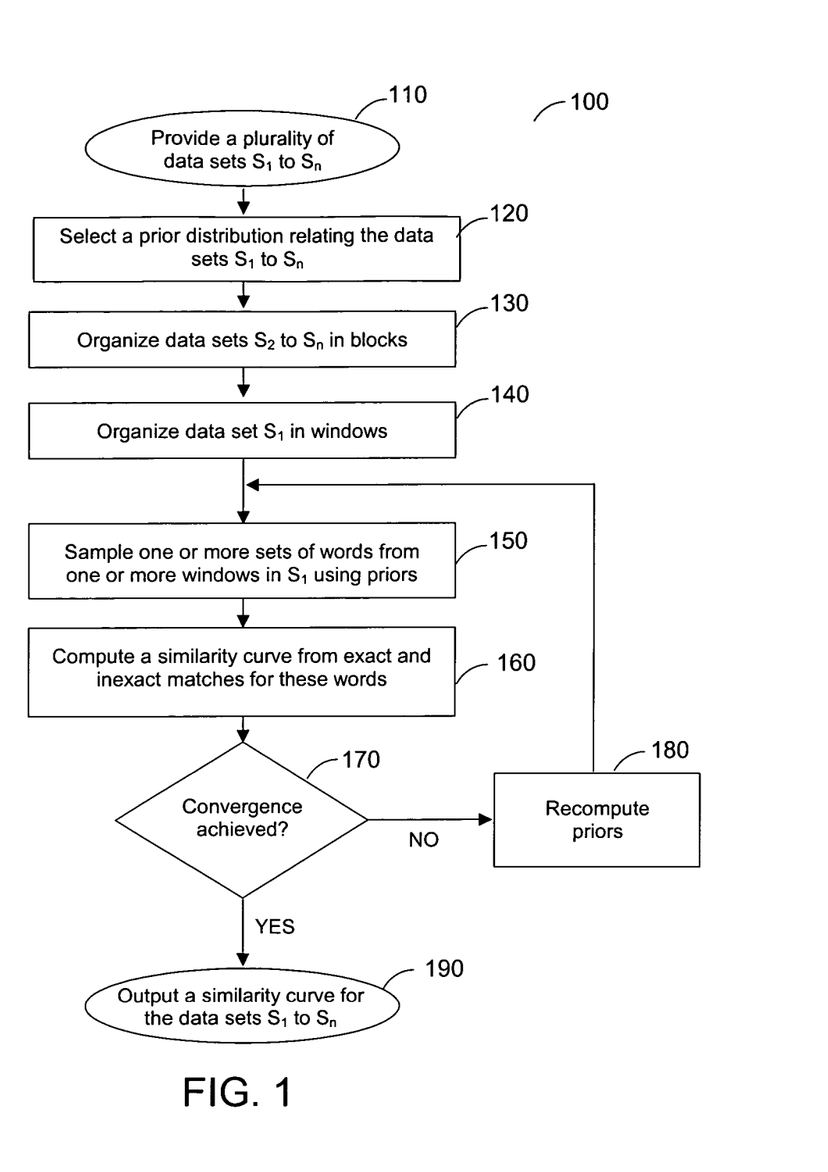
FIG. 1 is a general flowchart of certain exemplary embodiments of the present invention.

An exemplary flow diagram of a method 100 according to exemplary embodiments of the present invention is shown in FIG. 1. Sequences $S_1$ and $S_2$ to $S_n$ which are to be compared may be read from a database (step 110). A distribution of priors relating $S_1$ and $S_2$ to $S_n$ may then be chosen (step 120). The sequences $S_2$ to $S_n$ can be organized into blocks (step 130). The words corresponding to these blocks may be stored in a searchable data structure. The sequence $S_1$ can then be organized into windows (step 140). This can allow a set of words or mers to be sampled rapidly from each window. One or more sets of words from $S_1$ may then be sampled (step 150). Predetermined parameters may be used to choose the words used in this step. A similarity curve, which may be based on identification of exact and inexact matches of these words, can then be calculated with respect to $S_2$ to $S_n$ (step 160). Priors may be used to determine the local similarity levels. The desired convergence of the process may then be evaluated (step 170). If convergence is not achieved, then the priors may then be updated based on the calculated results (step 180). Further sets of words from $S_1$ may then be sampled (step 150), and exact and inexact matches can again be calculated (step 160). If convergence is achieved, local similarity levels between the sequences $S_1$ and $S_2$ to $S_n$ may be provided as output (step 190).

Figure 2:
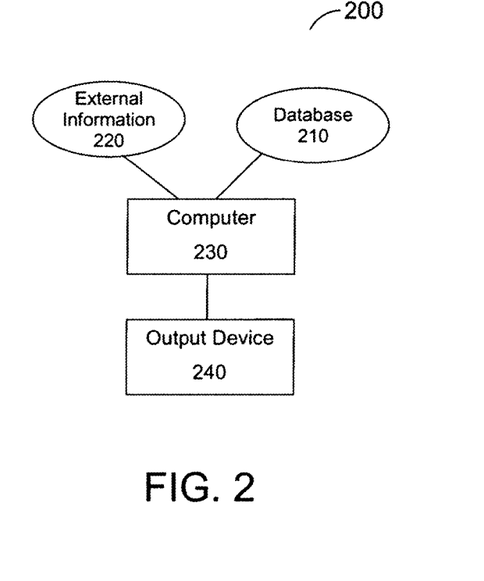
FIG. 2 is a schematic diagram of a system in accordance with certain exemplary embodiments of the present invention.

An exemplary embodiment of a system for implementing the present invention is shown in FIG. 2. For example, a database 210 may contain two or more sequences to be compared. These sequences may include genetic sequences, text strings, computer code, etc. The system may further comprise and/or utilize external information 220, which can include, e.g., domain-dependent knowledge or statistical models that relates to the sequences that are to be compared, as well as algorithms that may be used to conduct searches of the sequences to detect various types of matches. The external information 220 and information contained in the database 210 can be communicated to a computer 230. The computer 230 may be configured, e.g., to calculate matches and/or local regions of similarity between the sequences. Similarity regions and other information relating to the sequences being compared may be communicated to an output device 240. The output device 240 may comprise any suitable display device, including but not limited to a video monitor, a printer, a data storage medium, and the like. The computer 230 can include a hard drive, CD ROM, RAM, and/or other storage devices or media which can include thereon software, which can be configured to execute the exemplary embodiments of the method of the present invention.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. In addition, all publications referenced above are incorporated herein by reference in their entireties.

What is claimed is:

1. A method for obtaining information associated with a sequence similarity across a plurality of regions among a plurality of strings, comprising:
   (a) receiving a particular string and at least one further string, wherein at least one of the particular string or the at least one further string is ordered;
   (b) organizing the particular string into the regions;
   (c) generating a plurality of subregions corresponding to a sample of the regions;
   (d) obtaining particular information related to at least one of an initially unknown or guessed-at predetermined statistical distribution of local variations in the sequence similarity;
   (e) using a processing arrangement, automatically determining local variations in the sequence similarity across the subregions with respect to the at least one further string based on the particular information;
   (f) using the processing arrangement, modifying the particular information based on the determined local variations in sequence similarity;
   (g) repeating procedures (e) and (f) until a preselected criterion is met; and
   (h) at least one of storing the particular information in a storage arrangement in at least one of a user-accessible format or a user-readable format or displaying the particular information on a hardware display,
   wherein the particular information is provided in a form of a sequence similarity curve that includes a highest similarity of a particular subregion of the subregions at a particular position in the particular string compared to a further subregion of all positions in the at least one further string, and wherein a computational time utilized to perform procedures (e) to (g) is linearly proportional to a size of at least one of the particular string or the at least one further string.

2. The method according to claim 1, wherein the particular string and the at least one further string have a form of a linear sequence.

3. The method according to claim 1, wherein the particular information is domain-dependent.

4. The method according to claim 3, wherein the particular information is based on at least one of (i) an independent string that is different from the particular string and the at least one further string, or (ii) a statistical model related to at least one of the particular string or the at least one further string.

5. The method according to claim 4, wherein the determining procedure further comprises the subprocedure of verifying the local variations in sequence similarity based on the computational time.

6. The method according to claim 5, wherein the verifying subprocedure comprises comparing the local variations in sequence similarity and the particular information.

7. The method according to claim 1, further comprising providing regions of predetermined sequence similarity in the particular string with respect to the at least one further string.

8. The method according to claim 1, wherein the sequence similarity is determined based on a number of exact matches and inexact matches of the subregions with respect to the at least one further string.

9. The method according to claim 8, wherein the subregions comprise at least one of words or mers.

10. The method according to claim 1, wherein the particular information is provided in a further form of at least one of a statistical prior distribution, a hierarchal prior model, a uniform distribution, or a homology curve.

11. The method according to claim 1, wherein the particular information is based on a statistical model of at least one of edit operations or mutations.

12. The method according to claim 1, wherein the particular subregions are selected based on the particular information.

13. The method according to claim 12, wherein the determining procedure further comprises detecting exact matches and inexact matches of the particular subregions with respect to subregions of the at least one further string.

14. The method according to claim 12, wherein the particular subregions of the particular string have the form of a set of windows.

15. The method according to claim 14, wherein the particular subregions are arranged into subgroups, and wherein the determining procedure comprises comparing each particular subregion associated with the subgroups to further subregions of the at least one further string to detect at least one of (i) an exact match, (ii) an inexact match comprising a single error, or (iii) an inexact match comprising two errors between the particular subregion and the further subregions.

16. The method according to claim 14, wherein subregions of the at least one further string have a form of a set of blocks.

17. The method according to claim 16, wherein the set of blocks has a form of at least one of a hash table or a suffix array.

18. The method according to claim 1, wherein the modifying procedure comprises using at least one of a Bayesian technique, a Bayesian technique together with a boosting technique, or a Bayesian estimator.

19. The method according to claim 1, wherein the determining procedure is performed using a Bayesian estimator.

20. The method according to claim 1, wherein the determining procedure comprises associating at least one of a mean, a standard deviation or a confidence data with each of the regions.

21. The method according to claim 1, wherein the determining procedure further comprises the subprocedure of generating a local alignment data based on the local variations in the sequence similarity.

22. The method according to claim 1, wherein the preselected criterion comprises at least one of a total computational time, a total number of executions of the repeating procedure, or a preselected change in the determined local variations in sequence similarity between iterations of procedures (e)-(g).

23. The method according to claim 1, wherein the particular string and the at least one further string have a form of entire genome sequences.

24. The method according to claim 1, wherein the particular string and the at least one further string have a form of at least one of a webpage code listing, a weblog, or a computer code listing.

25. The method according to claim 1, wherein the particular string and the at least one further string have a form of at least one of a natural-language text, a times-series string, speech, an image, or video data.

26. The method according to claim 1, wherein the particular string comprises at least one of a genome sequence of nucleotides, a short sequence of amino acids, natural-language text, natural-generated text, computer-generated text, hypertext, a weblog, blog, network log, or computer scripts, source code or object code.

27. The method according to claim 1, wherein the sequence similarity curve further includes the highest similarity of the particular subregion at at least one further particular position in the particular string compared to the particular subregion of all of the positions in the at least one further string.

28. The method according to claim 1, wherein the particular subregion has a particular length.

29. A system for determining information associated with a sequence similarity across a plurality of regions among a plurality of strings, comprising:
a non-transitory computer-readable medium which includes thereon a set of instructions, wherein the set of instructions are configured to program a processing arrangement to:
(a) receive a particular string and at least one further string, wherein at least one of the particular string or the at least one further string is ordered;
(b) organize the particular string into the regions;
(c) generate a plurality of subregions corresponding to a sample of the regions;
(d) obtain particular information related to at least one of an initially unknown or guessed-at predetermined statistical distribution of local variations in the sequence similarity,
(e) determine local variations in the sequence similarity across the subregions with respect to the at least one further string based on the particular information;
(f) modify the particular information based on the determined local variations in sequence similarity;
(g) repeat procedures (e) and (f) until a preselected criterion is met; and
(h) at least one of storing the particular information in a storage arrangement in at least one of a user-accessible format or a user-readable format or displaying the particular information on a hardware display;
wherein the particular information is provided in a form of a sequence similarity curve that includes a highest similarity of a particular subregion of the subregions at a particular position in the particular string compared to a further subregion of all positions in the at least one further string, and wherein a computational time utilized to perform procedures (e) to (g) is linearly proportional to a size of at least one of the particular string or the at least one further string.

30. The method according to claim 29, wherein the sequence similarity curve further includes the highest similarity of the particular subregion at at least one further particular position in the particular string compared to the particular subregion of all of the positions in the at least one further string.

31. The system according to claim 29, wherein the particular subregion has a particular length.

32. A non-transitory computer-readable medium which includes thereon a software arrangement for determining information associated with a sequence similarity across plurality of regions among a plurality of strings, the software arrangement comprising:
a first set of instructions which, when executed by a processing arrangement, is configured to receive a particular string and at least one further string, wherein at least one of the particular string or the at least one further string is ordered;
a second set of instructions which, when executed by a processing arrangement, is configured to organize the particular string into the regions;
a third set of instructions which, when executed by a processing arrangement, is configured to generate a plurality of subregions corresponding to a sample of the regions;
a fourth set of instructions which, when executed by the processing arrangement, is configured to obtain particular information related to at least one of an initially unknown or guessed-at predetermined statistical distribution of the local variations in the sequence similarity;
a fifth set of instructions which, when executed by the processing arrangement, is configured to determine local variations in the sequence similarity across the with respect to the at least one further string based on the particular information;
a sixth set of instructions which, when executed by the processing arrangement, is configured to modify the particular information based on the determined local variations in the sequence similarity;
a seventh set of instructions which, when executed by the processing arrangement, is configured to repeat execution of the fifth and sixth sets of instructions until a preselected criterion is met; and
an eighth set of instructions which, when executed by the processing arrangement, is configured to at least one of store the particular information in a storage arrangement in at least one of a user-accessible format or a user-readable format or display the particular information on a hardware display;
wherein the particular information is provided in a form of a sequence similarity curve that includes a highest similarity of a particular subregion of the subregions at a particular position in the particular string compared to a further subregion of all positions in the at least one further string, and wherein the fifth, sixth and seventh sets of instructions, when executed by the processing arrangement, are performed utilizing a computational time that is linearly proportional to a size of at least one of the particular string or the at least one further string.

33. The method according to claim 32, wherein the sequence similarity curve further includes the highest similarity of the particular subregion at at least one further particular position in the particular string compared to the particular subregion of all of the positions in the at least one further string.

34. The computer-readable medium according to claim 32, wherein the particular subregion has a particular length.

35. A method for obtaining information associated with a sequence similarity across a plurality of regions among a plurality of strings, comprising:
(a) receiving a particular string and at least one further string, wherein at least one of the particular string or the at least one further string is non-random and specifically ordered;
(b) organizing the particular string into the regions;
(c) generating a plurality of subregions corresponding to a sample of the regions;
(d) obtaining particular information related to a predetermined statistical distribution of local variations in the sequence similarity;
(e) using a processing arrangement, automatically determining local variations in the sequence similarity across the subregions with respect to the at least one further string based on the particular information;
(f) using the processing arrangement, modifying the particular information based on the determined local variations in sequence similarity;
(g) repeating procedures (e) and (f) until a preselected criterion is met; and
(h) at least one of storing the particular information in a storage arrangement in at least one of a user-accessible format or a user-readable format or displaying the particular information on a hardware display,
wherein the particular information is provided in a form of a sequence similarity curve that includes a highest similarity of a particular subregion of the subregions at a particular position in the particular string compared to a further subregion of all positions in the at least one further string, and wherein the computational time utilized to perform procedures (e) to (g) is linearly proportional to a size of at least one of the particular string or the at least one further string.

36. The method according to claim 35, wherein the sequence similarity curve further includes the highest similarity of the particular subregion at at least one further particular position in the particular string compared to the particular subregion of all of the positions in the at least one further string.

37. The method according to claim 35, wherein the particular subregion has a particular length.

38. A system for determining information associated with a sequence similarity across a plurality regions among a plurality of strings, comprising:
a non-transitory computer-readable medium which includes thereon a set of instructions, wherein the set of instructions are configured to program a processing arrangement to:
(a) receive a particular string and at least one further string, wherein at least one of the particular string or the at least one further string is non-random and specifically ordered;
(b) organize the particular string into the regions;
(c) generate a plurality of subregions corresponding to a sample of the regions;
(d) obtain particular information related to a predetermined statistical distribution of local variations in the sequence similarity;
(e) determine local variations in the sequence similarity across the subregions with respect to the at least one further string based on the particular information;
(f) modify the particular information based on the determined local variations in sequence similarity;
(g) repeat procedures (e) and (f) until a preselected criterion is met; and
(h) at least one of storing the particular information in a storage arrangement in at least one of a user-accessible format or a user-readable format or displaying the particular information on a hardware display;
wherein the particular information is provided in a form of a sequence similarity curve that includes a highest similarity of a particular subregion of the subregions at a particular position in the particular string compared to a further subregion of all positions in the at least one further string, and wherein the set of instructions are further configured to program the processing arrangement to perform procedures (e) through (g) utilizing a computational time that is linearly proportional to a size of at least one of the particular string or the at least one further string.

39. The method according to claim 38, wherein the sequence similarity curve further includes the highest similarity of the particular subregion at at least one further particular position in the particular string compared to the particular subregion of all of the positions in the at least one further string.

40. The system according to claim 38, wherein the particular subregion has a particular length.

41. A non-transitory computer-readable medium which includes thereon a software arrangement for determining information associated with a sequence similarity across a plurality of regions among a plurality of strings, the software arrangement comprising:
a first set of instructions which, when executed by a processing arrangement, is configured to receive a particular string and at least one further string, wherein at least one of the particular string or the at least one further string is non-random and specifically ordered;
a second set of instructions which, when executed by a processing arrangement, is configured to organize the particular string into the regions;
a third set of instructions which, when executed by a processing arrangement, is configured to generate a plurality of subregions corresponding to a sample of the regions;
a fourth set of instructions which, when executed by the processing arrangement, is configured to obtain particular information related to a predetermined statistical distribution of the local variations in the sequence similarity;
a fifth set of instructions which, when executed by the processing arrangement, is configured to determine local variations in the sequence similarity across the subregions with respect to the at least one further string based on the particular information;
a sixth set of instructions which, when executed by the processing arrangement, is configured to modify the particular information based on the determined local variations in the sequence similarity;
a seventh set of instructions which, when executed by the processing arrangement, is configured to repeat execution of the fifth and sixth sets of instructions until a preselected criterion is met; and
an eighth set of instructions which, when executed by the processing arrangement, is configured to at least one of store the particular information in a storage arrangement in at least one of a user-accessible format or a user-readable format or display the particular information on a hardware display;

wherein the particular information is provided in a form of a sequence similarity curve that includes a highest similarity of a particular subregion of the subregions at a particular position in the particular string compared to a further subregion of all positions in the at least one further string, and wherein the fifth, sixth and seventh sets of instructions, when executed by the processing arrangement, are performed utilizing a computational time that is linearly proportional to a size of at least one of the particular string or the at least one further string.

42. The method according to claim 41, wherein the sequence similarity curve further includes the highest similarity of the particular subregion at at least one further particular position in the particular string compared to the particular subregion of all of the positions in the at least one further string.

43. The method according to claim 41, wherein the particular subregion has a particular length.

* * * * *